US010405943B2

(12) United States Patent
Baldwin

(10) Patent No.: US 10,405,943 B2
(45) Date of Patent: Sep. 10, 2019

(54) KIT AND METHOD FOR REDUCED RADIATION PROCEDURES

(71) Applicant: FACULTY PHYSICIANS AND SURGEONS OF LOMA LINDA UNIVERSITY SCHOOL OF MEDICINE, Loma Linda, CA (US)

(72) Inventor: Dalton Duane Baldwin, Loma Linda, CA (US)

(73) Assignee: FACULTY PHYSICIANS AND SURGEONS OF LOMA LINDA UNIVERSITY SCHOOL OF MEDICINE, Loma Linda, CA (US)

( * ) Notice: Subject to any disclaimer, the term of this patent is extended or adjusted under 35 U.S.C. 154(b) by 185 days.

(21) Appl. No.: 15/271,414

(22) Filed: Sep. 21, 2016

(65) Prior Publication Data

US 2017/0095314 A1 Apr. 6, 2017

Related U.S. Application Data

(60) Provisional application No. 62/222,037, filed on Sep. 22, 2015.

(51) Int. Cl.

*A61B 90/00* (2016.01)
*A61M 25/09* (2006.01)

(Continued)

(52) U.S. Cl.

CPC .............. *A61B 90/39* (2016.02); *A61B 1/307* (2013.01); *A61B 6/12* (2013.01); *A61B 8/0841* (2013.01);

(Continued)

(58) Field of Classification Search

None

See application file for complete search history.

(56) References Cited

U.S. PATENT DOCUMENTS

| | | | |
|---|---|---|---|
| 3,801,205 | A | 4/1974 | Eggenschwyler |
| 4,319,839 | A | 3/1982 | Durran |

(Continued)

FOREIGN PATENT DOCUMENTS

| | | | |
|---|---|---|---|
| JP | 2002510997 | | 4/2002 |
| WO | 9315683 | A1 | 8/1993 |
| WO | 2014197502 | A1 | 12/2014 |

OTHER PUBLICATIONS

Sodickson, A., Baeyens, P. F., Andriole, K. P. et al., Recurrent CT, cumulative radiation exposure, and associated radiation-induced cancer risks from CT of adults. Radiology, 251: 175-184, Apr. 2009.

(Continued)

*Primary Examiner* — Brian T Gedeon
(74) *Attorney, Agent, or Firm* — Novel IP

(57) ABSTRACT

A kit for performing a reduced radiation percutaneous procedure is provided. The kit includes a needle access device having a needle connected to a hub portion having an opaque cap portion, a non-opaque body portion positioned between the opaque cap portion and the needle, and a channel extending through the opaque cap portion; a sticker having an adhesive side adapted to adhere to the skin of a patient, and a display surface opposite the adhesive side configured to enhance visualization of the sticker in low light; and a guidewire having a floppy portion with a distal end, an intermediate region connected to the floppy portion, such that the intermediate region is less floppy than the floppy portion; and an ultrasonic-profile-enhancing feature disposed within 3 centimeters of the distal end of the floppy portion.

19 Claims, 13 Drawing Sheets

(51) Int. Cl.

| | |
|---|---|
| ***A61B 17/22*** | (2006.01) |
| ***A61M 25/10*** | (2013.01) |
| ***A61M 27/00*** | (2006.01) |
| ***A61B 6/12*** | (2006.01) |
| ***A61B 1/307*** | (2006.01) |
| ***A61B 34/20*** | (2016.01) |
| ***A61B 17/34*** | (2006.01) |
| ***A61M 5/158*** | (2006.01) |
| ***A61M 5/00*** | (2006.01) |
| ***A61B 8/08*** | (2006.01) |
| ***A61B 90/13*** | (2016.01) |

(52) U.S. Cl.

CPC .... *A61B 17/22012* (2013.01); *A61B 17/3403* (2013.01); *A61B 34/20* (2016.02); *A61B 90/13* (2016.02); *A61M 5/002* (2013.01); *A61M 5/007* (2013.01); *A61M 5/158* (2013.01); *A61M 25/09* (2013.01); *A61M 25/09041* (2013.01); *A61M 25/10* (2013.01); *A61M 27/00* (2013.01); *A61B 2017/22014* (2013.01); *A61B 2017/3413* (2013.01); *A61B 2034/2068* (2016.02); *A61B 2090/395* (2016.02); *A61B 2090/3925* (2016.02); *A61B 2090/3937* (2016.02); *A61B 2090/3941* (2016.02); *A61B 2090/3966* (2016.02); *A61B 2090/3991* (2016.02); *A61B 2090/3995* (2016.02); *A61M 2005/1586* (2013.01); *A61M 2005/1588* (2013.01)

(56) References Cited

U.S. PATENT DOCUMENTS

| | | | | |
|---|---|---|---|---|
| 4,651,732 | A | 3/1987 | Frederick | |
| 4,674,870 | A | 6/1987 | Cain | |
| 4,803,976 | A | 2/1989 | Frigg | |
| 5,409,000 | A | 4/1995 | Imran | |
| 5,810,841 | A | 9/1998 | McNeirney | |
| 6,021,342 | A | 2/2000 | Brabrand | |
| 6,041,249 | A | 3/2000 | Regn | |
| 6,096,049 | A | 8/2000 | McNeirney | |
| 6,443,960 | B1 | 9/2002 | Brabrand | |
| 6,605,095 | B2 | 8/2003 | Grossman | |
| 6,607,477 | B1 | 8/2003 | Longton | |
| 6,689,142 | B1 | 2/2004 | Tremaglio, Jr. | |
| 6,810,595 | B2 | 11/2004 | Chan | |
| 7,204,826 | B2 | 4/2007 | Tremaglio | |
| 7,621,868 | B2 | 11/2009 | Breidenthal | |
| 7,766,878 | B2 | 8/2010 | Tremaglio, Jr. | |
| 7,876,942 | B2 * | 1/2011 | Gilboa | A61B 6/12 382/128 |
| 8,162,852 | B2 | 4/2012 | Norris | |
| 8,454,586 | B2 | 6/2013 | Anastasie | |
| 8,715,233 | B2 | 5/2014 | Brewer | |
| 8,998,943 | B2 | 4/2015 | Baldwin | |
| 9,095,361 | B2 | 8/2015 | Baldwin | |
| 9,351,758 | B2 | 5/2016 | Baldwin | |
| 9,918,739 | B2 | 3/2018 | Baldwin | |
| 10,010,374 | B2 * | 7/2018 | Besser | A61B 34/20 |
| 10,085,767 | B2 | 10/2018 | Baldwin | |
| 2003/0120154 | A1 | 6/2003 | Sauer | |
| 2004/0103903 | A1 | 6/2004 | Falahee | |
| 2004/0106934 | A1 | 6/2004 | Grossman | |
| 2004/0122311 | A1 * | 6/2004 | Cosman | A61B 6/5247 600/427 |
| 2005/0256451 | A1 | 11/2005 | Adams | |
| 2007/0100234 | A1 | 5/2007 | Arenson | |
| 2007/0100299 | A1 | 5/2007 | Magnusson | |
| 2007/0106231 | A1 | 5/2007 | Snow | |
| 2008/0146915 | A1 | 6/2008 | McMorrow | |
| 2008/0146939 | A1 | 6/2008 | McMorrow | |
| 2008/0200876 | A1 | 8/2008 | Kukuk | |
| 2010/0099980 | A1 | 4/2010 | Godara | |
| 2011/0172520 | A1 | 7/2011 | Lentz | |
| 2012/0022504 | A1 | 1/2012 | Epshtein | |
| 2012/0022508 | A1 | 1/2012 | Gross | |
| 2012/0123204 | A1 | 5/2012 | Wynberg | |
| 2012/0143224 | A1 * | 6/2012 | Chan | A61B 17/0482 606/148 |
| 2012/0316500 | A1 | 12/2012 | Bierman | |
| 2013/0018254 | A1 | 1/2013 | Drucker | |
| 2014/0005604 | A1 | 1/2014 | Murphy | |
| 2014/0107473 | A1 | 4/2014 | Dumoulin | |
| 2014/0236019 | A1 * | 8/2014 | Rahum | A61B 5/0075 600/473 |
| 2014/0301699 | A1 * | 10/2014 | Goldfarb | A61B 1/00126 385/43 |
| 2014/0357986 | A1 | 12/2014 | Baldwin | |
| 2014/0357987 | A1 * | 12/2014 | Baldwin | A61B 5/065 600/424 |
| 2015/0272701 | A1 | 10/2015 | Baldwin | |
| 2017/0095314 | A1 | 4/2017 | Baldwin | |
| 2017/0303940 | A1 | 10/2017 | Sperry | |

OTHER PUBLICATIONS

Supplementary European Search Report for EP14807718, dated Dec. 5, 2016.

International Search Report for PCT/US16/52755, dated Dec. 30, 2016.

European Search Report for European Application No. EP18161332, dated Sep. 10, 2018.

Notice of Reasons for Rejection for JP2016518415, dated Apr. 9, 2018.

Decision of Rejection for JP2016518415, dated Oct. 30, 2018.

International Search Report for PCT/US14/40744, dated Oct. 12, 2014.

International Preliminary Report on Patentability for PCT/US14/40744, dated Oct. 12, 2014.

Bilen, et al: "Laser-Assisted Fluoroscopic Puncture: A New Technique for Accessing the Kidney", Journal of Endourology, vol. 17, No. 7, Sep. 2003.

Blair, et al.: "Reduced Fluoroscopy Protocol for Percutaneous Nephrostolithotomy: Feasibility, Outcomes and Effects on Fluoroscopy Time", The Journal of Urology, vol. 190, Dec. 2013, pp. 2112-2116.

Brisbane, et al.: "Fluoro-less Ureteral Stent Placement Following Uncomplicated Ureteroscopic Stone Removal: A Feasibility Study", Urology 80 (4), 2012, pp. 766-770.

Greene, et al.: "Comparison of a Reduced Radiation Fluoroscopy Protocol to Conventional Fluoroscopy during Uncomplicated Ureteroscopy", Urology 79 (2), 2011, pp. 287-290.

Hsi, et al.: "Fluoroless Ureteroscopy: Zero-Dose Fluoroscopy During Ureteroscopic Treatment of Urinary-Tract Calculi", Journal of Endourology, vol. 27, No. 4, Apr. 2013, pp. 432-437.

Ko, et al.: "C-Arm Laser Positioning Device to Facilitate Percutaneous Renal Access", Surgeon's Workshop, Urology 70 (2), 2007.

Kokorowski, et al.: "Prospective Systematic Intervention to Reduce Patient Exposure to Radiation During Pediatric Ureteroscopy", The Journal of Urology, vol. 190, 1474-1478, Oct. 2013.

Kroes, et al.: "Assessment of Needle Guidance Devices for Their Potential to Reduce Fluoroscopy Time and Operator Hand Dose during C-Arm Cone-Beam Computed Tomography-guided Needle Interventions", J Vasc Interv Radiol, Jun. 2013; 24:901-906.

Krupp, et al.: "Fluoroscopic Organ and Tissue-Specific Radiation Exposure by Sex and Body Mass Index During Uretereoscopy", Journal of Endourology, vol. 24, No. 7, Jul. 2010, pp. 1067-1073.

Nguyen, et al.: "In Automated Fluoroscopy Settings, Does Shielding Affect Radiation Exposure to Surrounding Unshielded Tissues?", Journal of Endourology, vol. 26, No. 11, Nov. 2012.

Shuler et al.: "Laser Targeting With C-Arm Fluoroscopy: Effect on Image Acquisition and Radiation Exposure", J Orthop Trauma, vol. 27, No. 5, May 2013. pp. e97-e102.

Smith, et al.: "Radiation Exposure During Continuous and Pulsed Fluoroscopy", Journal of Endourology, vol. 27, No. 3, Mar. 2013, pp. 384-388.

(56) References Cited

OTHER PUBLICATIONS

Office Action dated Dec. 31, 2015 for U.S. Appl. No. 14/802,753.
Hawkins et al. "Combined Retrograde/Antegrade Nephrostomy Technique," 1987, Journal of Endourology, vol. 1, No. 4, pp. 235-241.
Office Action dated Sep. 20, 2016 for U.S. Appl. No. 14/802,753.
Notice of Allowance dated Nov. 7, 2017 for U.S. Appl. No. 14/802,753; (pp. 1-5).
Preinterview First Office Action dated Aug. 29, 2014 for U.S. Appl. No. 14/295,148.
International Search Report and Written Opinion, re PCT App. No. PCT/US2014/040744, dated Oct. 12, 2014.
Office Action dated Jan. 16, 2015 for U.S. Appl. No. 14/295,148.
Office Action dated Sep. 27, 2017 for U.S. Appl. No. 15/145,631.
Preinterview First Office Action dated Nov. 11, 2014 for U.S. Appl. No. 14/295,224.
International Search Report for PCT/US18/29550, dated Jul. 30, 2018.

* cited by examiner 100
103
106

100

KIT AND METHOD FOR REDUCED RADIATION PROCEDURES

CROSS-REFERENCE TO RELATED APPLICATIONS

The present application relies on, for priority, U.S. Patent Provisional Application No. 62/222,037, entitled "Kit for Reduced Radiation Procedures" and filed on Sep. 22, 2015, which is herein incorporated by reference in its entirety.

The present application relates to U.S. Pat. No. 9,095,361, entitled "METHODS AND APPARATUSES FOR FLUORO-LESS OR NEAR FLUORO-LESS PERCUTANEOUS SURGERY ACCESS," and filed on Jun. 3, 2014, which is also herein incorporated by reference in its entirety.

FIELD

The present specification relates to devices and kits for percutaneous surgery access and more specifically to needle placement procedures and devices that minimize or eliminate the use of fluoroscopy, in order to minimize radiation exposure.

BACKGROUND

Percutaneous access is a commonly used step for the treatment and the testing of a variety of diseases and conditions in a plethora of surgical and clinical procedures. An initial step in many forms of percutaneous surgery is the insertion of a wire for later access into the inner portion of a lumen, space, viscous, or organ. An example of this type of access could be placement of a needle through the skin into the kidney for access into one of the calices of the kidney for removing kidney stones, such as in a percutaneous nephrolithotomy (PCNL) procedure. This step of the percutaneous procedure is often one of the most difficult steps and often requires real-time, imaging guidance with ultrasound, CT, or fluoroscopy.

Conventional techniques for needle placement in PCNL can require the use of continuous fluoroscopy during the insertion of the needle into the collecting system. Due to the depth of the tissues surrounding the kidney and the variation of the renal position caused by ventilation the surgeon is asked to hit a small moving target positioned deep inside the body and slight imprecision in needle positioning may lead to complete failure to access the desired space. Subsequently, surgeons are required to grasp a needle using either their hands (placing their hands directly inside the fluoroscopy beam), or using a needle holder or device for holding the needle (decreasing their control and ability to perceive tactile subtle cues regarding tissue densities).

Fluoroscopy guidance accounts for a substantial percentage of the procedural radiation exposure to the patient as well as the surgical team. Every patient poses a different challenge and significant amounts of fluoroscopy can be used to navigate the trocar needle through the patient's anatomy. During needle placement, the amount of fluoroscopy required to obtain access is often several minutes and may be greater than 60 minutes of fluoroscopy time. Sixty minutes of fluoroscopy may be associated with significant radiation exposure and, depending upon the location of the fluoroscopy beam and the size of the patient, may exceed the recommended yearly occupational exposures of radiation. The deterministic effects of radiation occur quickly following exposure and may include sterility, cataracts, skin erythema, and damage to the blood production system, intestinal function, or neurologic function.

In contrast, the stochastic effects of radiation are not directly dose dependent and may occur at any time following radiation exposure and may include genetic damage, cancer, and mental effects. High levels of radiation exposure have been recognized as a potential carcinogenic risk to the patient since the high-energy radiation may cause DNA mutation. It has been shown that a few minutes of fluoroscopy time at standard settings will confer a 1/1,000 risk of developing fatal cancer. For every 1000 patients exposed to even 10 mSv of radiation, one of those will develop cancer as a result. Further, fluoroscopy exposure is also known to have a cumulative effect over time, increasing the risk of stochastic effects on both the patient and the staff members, including the physician. As there is no safe lower limit (no safe threshold), below which no risk for cancer will occur and since higher the exposure the greater the risk, it is important to decrease the radiation exposure of patients during percutaneous access.

Hence, there is need for needle placement procedures and devices that minimize or eliminate the use of fluoroscopy, in order to minimize radiation exposure. There is also need for devices and methods that would simplify surgical procedures and lower the costs associated with the same. Further, there is need for devices and methods of using the same that would reduce medical waste and the costs of disposal of this medical waste during and after a surgical procedure.

SUMMARY

In some embodiments, the present specification discloses a kit for performing a reduced radiation percutaneous procedure, the kit comprising: a needle access device comprising: a needle connected to a hub portion, the hub portion comprising: an opaque cap portion; a non-opaque body portion positioned between the opaque cap portion and the needle; and a channel extending through the opaque cap portion, the channel positioned such that the non-opaque body portion only illuminates when a light source is aligned with the channel; a sticker comprising: an adhesive side adapted to adhere to the skin of a patient; and a display surface opposite the adhesive side, the display surface being configured to enhance visualization of the sticker in low light, the sticker being configured to designate a portion of skin through which the needle should pass to be in alignment with a target site, wherein the sticker comprises an opening adapted to allow the needle to penetrate the portion of skin via the opening and not by penetrating a surface of the sticker; and a guidewire comprising: a flexible portion comprising a distal end; an intermediate region coupled to the flexible portion, wherein the intermediate region is more rigid than the flexible portion; and an ultrasonic-profile-enhancing feature disposed within 3 centimeters of the distal end of the flexible portion.

Optionally, the kit further comprises an item selected from the group consisting of a balloon catheter, a nephrostomy tube, an ultrasound contrast agent, and a stent.

Optionally, the item includes a feature to enhance the ultrasonic profile of the item.

Optionally, the kit is packaged in a single sterile pack.

Optionally, the display surface of the sticker comprises a glow-in-the-dark feature.

Optionally, the display surface of the sticker comprises a fluorescent material.

Optionally, the display surface of the sticker comprises a mirrored surface.

Optionally, the guidewire further comprises a mark on an outer surface of the guidewire, wherein the mark is configured to indicate a distance from a kidney to a ureteral orifice.

In some embodiments, the present specification discloses a method of performing a reduced radiation percutaneous access procedure, the method comprising: specifying a plurality of reduced radiation surgical items to include in a kit, wherein the kit comprises at least a portion of the plurality of surgical items packaged within a single sterile pack; and using at least one of the plurality of reduced radiation surgical items from the kit to perform a percutaneous procedure, wherein the percutaneous procedure comprises: identifying a target site within a kidney of a patient; aligning a laser with the target site; placing a sticker on a skin of a patient, wherein the sticker is adapted to indicate an area of skin through which a needle must pass to reach the target site when the needle is advanced along a line defined by the laser; inserting the needle and a cannula through the area of skin indicated by the sticker, the cannula coaxially surrounding the needle; advancing the needle and the cannula to the target site while keeping the needle in alignment with the line defined by the laser; and, withdrawing the needle from the cannula while leaving the cannula in place, thereby establishing a percutaneous access to the target site.

In some embodiments, the present specification discloses a method of performing a reduced radiation percutaneous access procedure, the method comprising: specifying a plurality of reduced radiation surgical items to include in a kit, wherein the kit comprises at least a portion of the plurality of reduced radiation surgical items packaged within a single sterile pack; and using at least one of the plurality of reduced radiation surgical items from the kit to perform a percutaneous procedure, wherein the percutaneous procedure comprises: identifying a target site within an organ of a patient; aligning a laser with the target site; placing a sticker on a skin of a patient, wherein the sticker is adapted to indicate an area of skin through which a needle must pass to reach the target site when the needle is advanced along a line defined by the laser; inserting the needle and a cannula through the area of skin indicated by the sticker, the cannula coaxially surrounding the needle; advancing the needle and the cannula to the target site while keeping the needle in alignment with the line defined by the laser; and, withdrawing the needle from the cannula while leaving the cannula in place, thereby establishing a percutaneous access to the target site.

Optionally, said plurality of reduced radiation surgical items to include in a kit can be selected from being selected from the group consisting of a guidewire, a needle, a sticker, a balloon catheter, a stent, a sheath, a contrast agent, and a basket catheter.

Optionally, said organ is a kidney.

Optionally, at least one of the plurality of reduced radiation surgical items includes a feature to enhance the ultrasonic profile of the item.

Optionally, the feature to enhance the ultrasonic profile of the item increases the roughness of a portion of a surface of the item relative to a remainder of said surface.

Optionally, the kit is packaged in a single sterile pack.

Optionally, a display surface of the sticker comprises a glow-in-the-dark feature.

Optionally, a display surface of the sticker comprises a fluorescent material.

Optionally, a display surface of the sticker comprises a mirrored surface.

Optionally, the guidewire further comprises a mark on an outer surface of the guidewire, wherein the mark is configured to indicate a distance from a kidney to a ureteral orifice.

In some embodiments, the present specification further discloses a method of making a kit for performing a reduced radiation percutaneous procedure, the method comprising receiving an order from a user, the order comprising a list of surgical items for performing a reduced radiation surgical procedure, the surgical items being selected from the group consisting of a guidewire, a needle, a sticker, a balloon catheter, a stent, a sheath, a contrast agent, and a basket catheter; and packaging into a single sterile pack at least two of the surgical items enumerated on the list.

The aforementioned and other embodiments of the present shall be described in greater depth in the drawings and detailed description provided below.

BRIEF DESCRIPTION OF THE DRAWINGS

These and other features and advantages of the present specification will be appreciated, as they become better understood by reference to the following detailed description when considered in connection with the accompanying drawings.

DETAILED DESCRIPTION

Figure 1C:
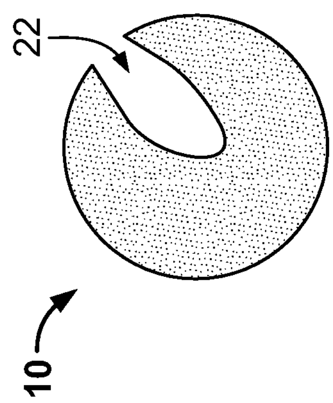
FIG. 1C illustrates the exemplary sticker having a recess adapted to allow needle access to a patient's skin, in accordance with an embodiment of the present specification.

The present specification relates to devices and kits for percutaneous surgery access and more specifically to needle placement procedures and devices that minimize or eliminate the use of fluoroscopy, in order to minimize radiation exposure.

The present specification is directed towards multiple embodiments. The following disclosure is provided in order to enable a person having ordinary skill in the art to practice the specification. Language used in this specification should not be interpreted as a general disavowal of any one specific embodiment or used to limit the claims beyond the meaning of the terms used therein. The general principles defined herein may be applied to other embodiments and applications without departing from the spirit and scope of the specification. Also, the terminology and phraseology used is for the purpose of describing exemplary embodiments and should not be considered limiting. Thus, the present specification is to be accorded the widest scope encompassing numerous alternatives, modifications and equivalents consistent with the principles and features disclosed. For purpose of clarity, details relating to technical material that is known in the technical fields related to the specification have not been described in detail so as not to unnecessarily obscure the present specification.

It should be noted herein that any feature or component described in association with a specific embodiment may be used and implemented with any other embodiment unless clearly indicated otherwise.

In various embodiments, reduced radiation percutaneous access is achieved by using needle placement procedures and devices that minimize or eliminate the use of fluoroscopy. Examples of devices that facilitate reduced radiation percutaneous access are discussed in U.S. Pat. No. 9,095,361, entitled "METHODS AND APPARATUSES FOR FLUORO-LESS OR NEAR FLUORO-LESS PERCUTANEOUS SURGERY ACCESS," filed on Jun. 3, 2014, which is included herein in its entirety.

In an embodiment, the present specification provides a reduced radiation kit comprising all or many of the instruments needed to perform a reduced radiation percutaneous procedure. In an embodiment, the reduced radiation kit comprises items selected by a user. The user may select the kit items based on the physiologic measurements of a patient, the technique to be practiced by a surgeon, or the resources available in the operating theatre.

In embodiments, the reduced radiation kit comprises the items packaged in a sterile manner ready for immediate use by the user. Having the items packed into a kit significantly reduces turnover times for operating room cases as the nurses do not need to open each item separately. Packaging items together is cheaper and simpler than opening up a separate package individually for each item. In addition, the reduced radiation kits reduce medical waste and the costs of disposal of this medical waste. In an embodiment, the user is required to attend a courses where the individual items are demonstrated, allowing the user to design one or more of the kits by selecting items of choice.

The reduced radiation kit of the present specification is used for different procedures requiring percutaneous access to different structures, lumens, organs, and spaces in the body, such as, but not limited to, the kidneys. Although the kit embodiments discussed herein are described with respect to removing kidney stones in a percutaneous nephrolithotomy (PCNL) procedure, the kit may be used for other procedures such as, but not limited to, placing probes into the kidney to treat a renal cancer, placing access into an infected fluid collection for drainage of an abscess, placing tubes into any space to serve as a drain, (i.e., pleural space, peritoneal drain, cholecystectomy drain, bladder drain, lymphocele drain, pericardial space, and such other procedures).

In an embodiment, the present specification provides a method of using a reduced radiation kit for performing percutaneous surgery such as, but not limited to, percutaneous needle access of an internal organ (e.g., kidney). For example, the methods, devices, and kits disclosed herein can be used to perform a percutaneous nephrolithotomy. In an embodiment, the present specification provides a method of obtaining percutaneous needle access by using the reduced radiation kit. The method comprises selecting a patient's calyx for percutaneous access; positioning a flexible ureteroscope in the selected calyx; directing a laser guide at a desired needle-insertion angle and in line with a tip of the ureteroscope; aligning a needle with the laser guide and the ureteroscope tip; and inserting the needle into the selected calyx. In an embodiment, if required, fluoroscopy is applied for less than ten seconds. In embodiments, method and reduced radiation kit of the present specification allows incremental reduction in radiation exposure of 5-10%. In an embodiment, this reduction ranges from 5% to 99%.

The method of obtaining percutaneous needle access also comprises delivering an instrument from the reduced radiation kit to the selected calyx. The instrument is configured to facilitate the insertion of the needle into the selected calyx. In an embodiment, the instrument is identifiable under ultrasound. In an embodiment, the instrument is one of a balloon catheter and a basket catheter.

Figure 1B:
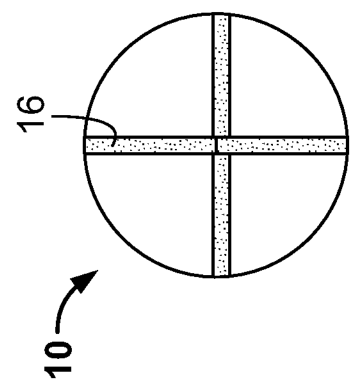
FIG. 1B illustrates the exemplary sticker having a marking on a display face, in accordance with an embodiment of the present specification.
Figure 1A:
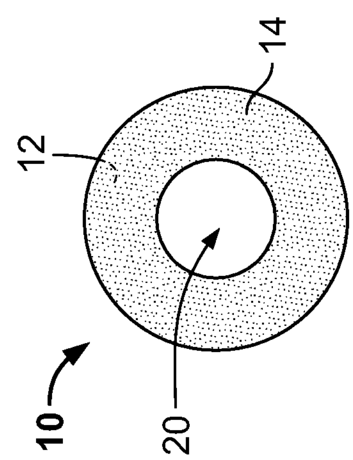
FIG. 1A illustrates an exemplary sticker provided in a reduced radiation kit, in accordance with an embodiment of the present specification.

In various embodiments, the items included in the reduced radiation kit are designed to facilitate reduced radiation percutaneous access. For example, as depicted in FIG. 1A-1C, the kit comprises one or more glow-in-the-dark stickers 10 or other indicators (e.g., a drawing marker, non-adhesive indicator, and the like). The sticker 10 comprises an adhesive on a back surface 12 of the sticker 10 and a display surface 14 opposite the back surface. The sticker 10 is configured to adhere to the skin of a patient. The display surface 14 of the sticker 10 is configured to enhance visualization in low light. In an embodiment, sticker 10 is used to identify the location of a patient's kidney. In an embodiment, the kit comprises a sticker 10 to identify the location of the bladder or another organ of the patient. Once the kidney is localized, one sticker may be placed at the location of the kidney and one sticker may be placed at the location of the bladder. In an embodiment, stickers 10 allow a fluoroscopy technician to identify the location of each area in the patient's body to save the radiation exposure usually required to localize a C-arm head being used to carry out the percutaneous access procedure. A laser pointer on the head of an image intensifier of the C-arm is used to target placement of the sticker 10. For example, after using the C-arm to generate an X-ray image and identifying the target location based on the image, a surgeon can mark the target using the sticker 10. The surgeon can direct the laser guide at the desired target based on the X-rays or other imaging techniques like ultrasound.

In an embodiment, sticker 10 comprises one or more marks 16 configured to allow an X-ray technician to easily identify a location of a patient's kidney. The one or more marks 16 may be configured in the form of a target (e.g., concentric circles, or cross-hairs). The marks 16 may comprise circles or rings like a target to facilitate correct positioning of the C-arm. In an embodiment, the mark 16 is coated with a glow-in-the-dark material to enhance visualization of the mark 16 in the dark. In an embodiment, all portions of the sticker 10 are made radiolucent except for some indicator that is dense such as a metal ring to allow easy visualization under fluoroscopy or metal crosshairs. In an embodiment, the sticker 10 comprises an opening 20 or recess 22 configured to allow a needle to penetrate the skin without penetrating the sticker 10. In an embodiment, sticker 10 is designed in the form of a ring, with the opening 20 being concentric with a surrounding portion of the sticker. The opening 20 may be off-center from the central portion of the sticker 10. In embodiments, the opening 20 may have a circular or non-circular shape.

In an embodiment, the surface of the sticker 10 comprises reflective material that, when properly configured, causes a laser beam to be reflected and to intensify when the laser is correctly aligned. In an embodiment, the sticker is made of a stainless steel material. Also, in an embodiment, the magnitude of laser reflection intensity is intensified by using batteries as an intensifying mechanism, along with ensuring precise alignment in order to provide a two-fold or four-fold increase in intensity.

The sticker 10 may be removed after positioning the C-arm to allow the needle to penetrate the skin without the needle penetrating through the sticker 10. In an embodiment, the sticker 10 comprises regions that are radiolucent. In another embodiment, the sticker 10 comprises circles that are radiodense to create a bulls-eye target when fluoroscopy is employed. In another embodiment, the sticker 10 is configured to have radiodense regions circumferentially surrounding radiolucent regions to create a target image when viewed under fluoroscopy. The glow-in-the-dark sticker and the mirrored sticker can be made radiolucent to allow X-ray beams to pass through the sticker 10 and thereby not interfere with visualization of the fluoroscopy image.

Figure 2:
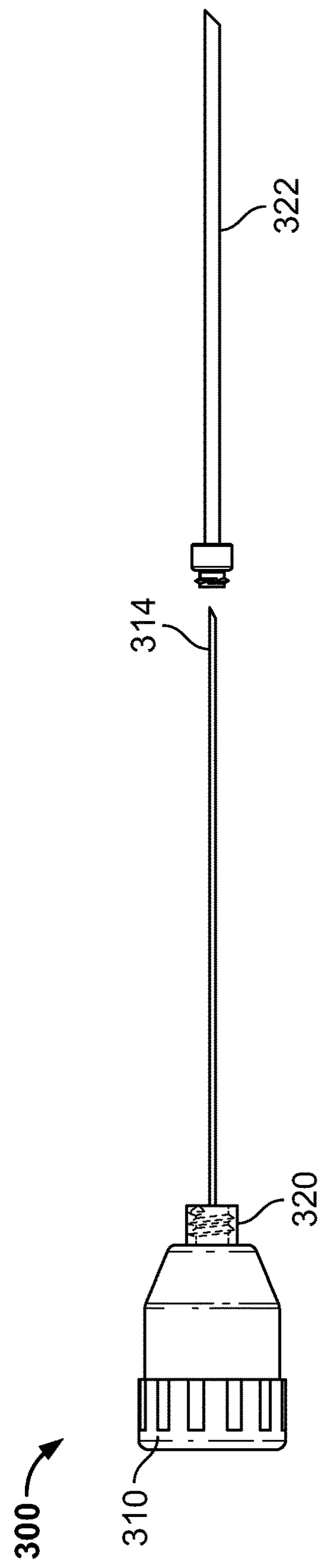
FIG. 2 illustrates an exemplary needle provided in the reduced radiation kit, in accordance with an embodiment of the present specification.

As shown in FIG. 2, the reduced radiation kit comprises a needle 300, in accordance with an embodiment of the present specification. In an embodiment, the kit comprises a reduced radiation device such as a laser Direct Alignment Reduced Radiation Technique (DARRT) needle. The needle 300 comprises any of the features of the needle described in U.S. Pat. No. 9,095,361, entitled "METHODS AND APPARATUSES FOR FLUORO-LESS OR NEAR FLUORO-LESS PERCUTANEOUS SURGERY ACCESS," filed on Jun. 3, 2014, which is incorporated herein in its entirety. In an embodiment, the needle 300 comprises a connector 320 (e.g., luer connector) to engage a cannula 322. After the needle-cannula assembly is inserted into a patient's skin, the connector 320 is disconnected and removed from the patient, while the cannula 322 maintains access into the patient. A user of the reduced radiation kit may select the needle 300 to be included in the kit.

Figure 2B:
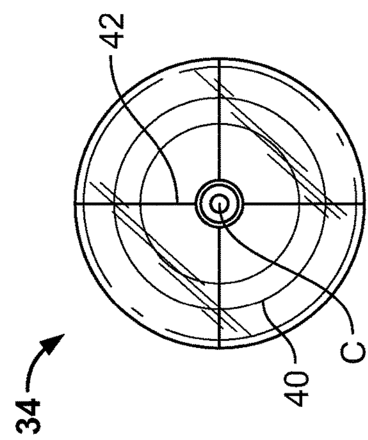
FIG. 2B illustrates a top view of the needle shown in FIG. 2A.
Figure 2A:
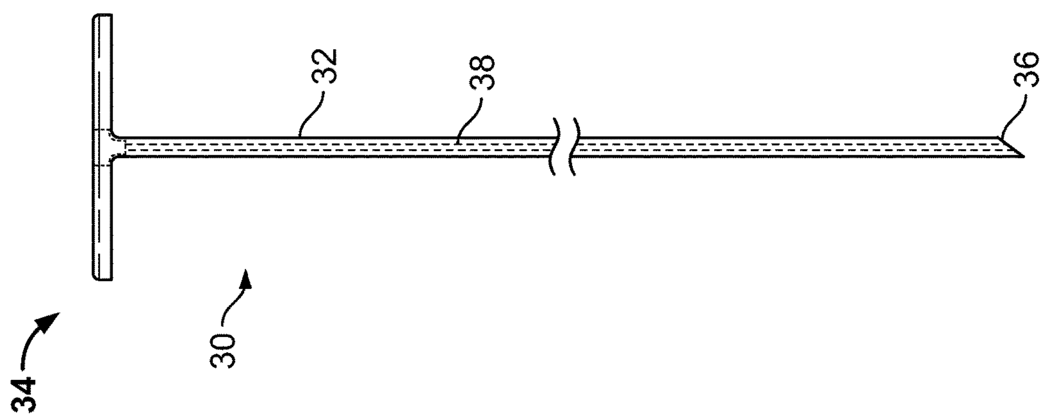
FIG. 2A illustrates an exemplary embodiment of a needle assembly that may be configured for use with the reduced radiation kit of the present specification.

FIG. 2A, 2B illustrate an exemplary embodiment of a needle assembly 30 that may be configured for use with the reduced radiation kit of the present specification. The needle 32 defines a lumen through which a stylet 38 optionally extends. The stylet 38 comprises a sharpened distal end to facilitate percutaneous access. The needle 32 comprises a blunt distal tip 36 to avoid inadvertent injury after removal of the stylet 38. In some embodiments, the distal tip of the needle 36 is sharpened. Optionally, the tip 36 of the needle 32 and/or stylet 38 is etched to create a prominent acoustic signal on ultrasound. In some embodiments, at least a portion of the needle 32 proximal to the tip 36 comprises a square shape to increase the acoustic prominence of the needle (not shown).

A proximal portion of the stylet 38 comprises a hub 34. In an embodiment, the hub 34 is disc-shaped (as shown in FIG. 2A). As shown in FIG. 2B, an upper surface of the hub 34 comprises a plurality of concentric rings 40 (e.g., two, three, or more) to help the surgeon accurately position a light guide source (e.g., laser). In some embodiments, at least a portion of the hub 34 (e.g., an outer portion of the hub 34 or the entire hub 34) is formed from a non-opaque material (e.g., transparent or translucent material). For example, an outer portion of the hub 34 is formed from a transparent material and a central portion of the hub 34 is formed from an opaque material to help center the laser. In some embodiments, the hub 34 has a diameter ranging between 1 cm and 5 cm. In an embodiment, the diameter of the hub 34 is approximately 2 cm.

In an embodiment, the distance between each ring 40 placed on the surface of the needle hub 34 is at least about 1 mm and/or less than or equal to about 10 mm, e.g., about 5 mm. The distance between each ring is substantially the same or may vary.

As shown in FIG. 2B, the hub 34 comprises a crosshatch 42 to help the user identify the central axis of the needle assembly 30. In some embodiments, the distance between the central axis C and an end of the crosshatch 42 ranges between 0.5 mm and 5.0 mm, or between 1.0 mm and 2.0 mm. In some embodiments, the distance between the central axis C and an end of the crosshatch 42 is one of 2 mm, and 1.5 mm.

Depending on the requirements of the procedure, the length of the needle 32 is at least 5 cm, at least or 10 cm or less than or equal to 20 cm. In some embodiments, the length of the needle 32 ranges between 5 cm and 20 cm, e.g., 10 cm, 15 cm, or 20 cm. In some embodiments, the diameter of the needle 32 is 12 gauge and/or less than or equal to 25 gauge, such as approximately 18 gauge. The needle 32 comprises a lumen configured to allow the passage of a wire between having a diameter ranging between 0.18 gauge and 0.38 gauge, such as approximately 0.25 gauge.

In embodiments, the hub 34 is transparent or translucent and comprises an opaque channel (not shown). In an embodiment, the opaque channel is centrally disposed in the hub 34. An upper surface of the hub 34 comprises an opening that allows the passage of the light source through the opaque channel when the opaque channel is aligned with the light source. In some embodiments, a width of the opaque channel ranges between 0.1 mm wide and 2 mm. In some embodiments, the opaque channel has a length ranging between 1 mm and 5 cm. The length to width ratio of the opaque channel is such that the angle that the needle 32 deviates from the axis of the light source and still produces the illumination of the glowing hub portion 34 of the needle 32 is very small angle, e.g., between 0.1 and 10 degrees, such as 2 degrees, and preferably less than 1 degree. In some embodiments, the opaque channel is lined with one or more reflectors. These reflectors are constructed from metal, glass, mirrors or any reflective material that can reflect light toward the light source when the light source is not aligned with the opaque channel so that no light enters the transparent or translucent portion of the hub 34. If the surgeon visualizes the feedback of the light reflected back out of the opaque channel, the surgeon would recognize that the orientation of the needle 32 is not correct. In some embodiments, the core of the channel is lined with a wound metal spring that reflects the light back out when not correctly aligned as described above.

In some embodiments, the needle assembly 30 comprises no stylet 38. The distal end 36 of the needle 32 comprises a sharpened end, and the hub 34 described above is coupled to a proximal end of the needle 32.

In an embodiment, the reduced radiation kit comprises a plurality of different needles of different lengths and gauges. In an embodiment, the kit comprises at least a 10 cm needle, a 15 cm needle, a 20 cm needle, or combinations thereof. In an embodiment, the kit comprises needles having diameters ranging from 18 gauge to 21 gauge for use in obtaining access for percutaneous kidney stone surgery and other such applications. In other embodiments, the kit comprises needles ranging from 1 cm to 40 cm in length and having diameters ranging from 14 gauge to 27 gauge, thereby allowing the kit to be used to access a variety of organs, structures, and sites in a patient's body.

In various embodiments, enhancing ultrasonic profile of a surgical instrument such as a guide wire or a needle is achieved by enhancing the echogenicity of the instrument, thereby making the instrument visible under ultrasound guidance. In an embodiment, ultrasound core biopsy needles for aspiration of breast tissues, prostate tissues, liver tissues, and the like comprise a polymeric coating wherein the coating is configured to enhance or increase echogenicity. In another embodiment, high purity alumina ($Al_2O_3$) powder dispersed in a matrix epoxy resin (a thermosetting polymer) is deposited on a metallic surface of an instrument using a spin coating process for increasing the instrument's visibility under ultrasound guidance. In another embodiment, etching or texturing a needle tip surface (creating a diffused, coarse surface) increases echogenic properties under ultrasound imaging, and aids in needle tip visualization under ultrasound guidance. In other embodiments, dimpling, scoring, roughening, and creating a serrated surface on the needle tip also aids in needle tip visualization under ultrasound guidance.

In various embodiments, techniques such as, but not limited to dip coating, spin coating, echogenic texturing, creating a roughened/diffused surface (via micro blasting, bead blasting), scoring, forming/bending, creating a pattern-embossed section, are used for increasing the ultrasonic profiles during an ultrasound-guided procedure of the guidewires and needles included in the reduced radiation kit. A roughened or diffused surface results in higher echogenicity because such a surface typically has many micro peaks and valleys, which, in turn, assist in increasing the surface's visibility during an ultra sound-guided procedure. Polymeric coating (dip coating or spin coating) enhances echogenicity of the coated surface (needles or guide wires) since such treatment with the appropriate coating material/compound creates a surface that is compatible with, and visible under ultrasound guidance at a molecular level. Collectively, such features which cause a surface to have an increased roughness relative to the remainder of the needle surface may be considered ultrasonic-profile-enhancing features.

Figures 3A, 3B, 3C:
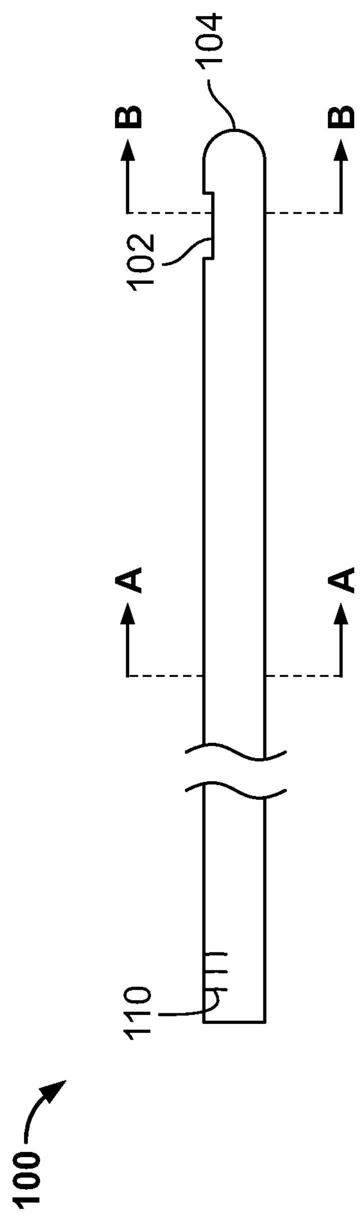
FIG. 3A illustrates a side view of an exemplary guidewire provided in the reduced radiation kit, in accordance with an embodiment of the present specification.
FIG. 3B is the transverse cross-sectional view of the guidewire along the line A-A indicated in FIG. 3A.
FIG. 3C is the transverse cross-sectional view of the guidewire along the line B-B indicated in FIG. 3B.

Referring to FIGS. 3A, 3B and 3C, the kit comprises a plurality of guidewires 100 with enhanced ultrasonic profiles. As is known, a guidewire is a thin, usually flexible wire that can be inserted into a confines or tortuous space to act as a guide for subsequent insertion of a stiffer or bulkier instrument. A guidewire may be used for entering obstructed vessels or channels in a human body, or may be used to assist in inserting, positioning and moving a catheter. Guidewires vary in size, length, stiffness, composition and shape of the tip. Various types of guidewires such as, but not limited to stiff wires, super stiff wires, wire comprising floppy portions/tips, wires coated for gliding smoothly, and wires having malleable tips are available and may be selected based on their application in a desired medical procedure.

Guidewires having a rounded cross section do not appear on ultrasound machines as the ultrasound waves go right past the rounded portions. However, guidewires having partial flat surfaces such as shown in FIGS. 3A and 3C are detectable by using ultrasound technique, as ultrasound bounce of a flat edge and are detected. Hence, in various embodiments, any portion of a guidewire and/or a needle included in the reduced radiation kit may be flattened, in order to increase their ultrasonic profile, thereby making said guidewires/needles visible when using ultrasound machines.

In an embodiment, guidewire 100 is a cylindrical wire having a circular cross-section as depicted in FIG. 3A. A guidewire 100 comprises a distal end 104, a proximal end 105 and at least one flat surface having a length 102 in close proximity to the distal end 104. The flat surface 102 reflects the sound waves emanating from an ultrasonic transducer. The flat surface 102 may be spaced away from the distal end 104 by a distance ranging from 1 cm to 5 cm for allowing ultrasonic localization of the guidewire distal end 104. In an embodiment, the length of the flat portion 102 as shown in FIG. 3A is approximately 5 mm; while a portion 103 that is flattened as shown in FIG. 3C does not exceed 10% of a total circumference of the guidewire. In an embodiment, guidewire 100 has a circular transverse cross-section over at least part of, at least a majority of, or substantially the entire guidewire, as shown in FIG. 3B. Additionally or alternatively, the guidewire 100 comprises an etching or a coating 106, as shown in FIG. 3C that allows the guidewire 100 to be easily seen under ultrasound, thereby facilitating ultrasound-guided placement, or placement at low mAs or kVp settings under fluoroscopy.

In an embodiment, the reduced radiation kit of the present specification may comprise a needle 300 (as shown in FIG. 2) having one or more features enhancing the ultrasonic profile of the needle 300. In an embodiment, similar to the guidewire 100 described above, the needle 300 may comprise a flat surface or an etching or coating that allows the needle 300 to be easily seen under ultrasound, thereby facilitating ultra-sound guided placement of the needle 300, or enabling needle guidance at low mA or kVp settings under fluoroscopy. In an embodiment, length of a flat portion (not shown in FIG. 2) included in a needle 300 is approximately 5 mm; while the portion that is flattened as does not exceed 10% of a total circumference of the needle. Also, in embodiments, the flat surface is spaced away from a distal tip of the needle 300 by a distance ranging from 1 cm to 5 cm for allowing ultrasonic localization of the needle tip.

In an embodiment, the guidewire 100 or needle 300 can be detected using single pulse fluoroscopic images using the lowest mA and kVp that provides an acceptable picture using intentionally fixed and reduced fluoroscopy settings. In an embodiment, the guidewire 100 is configured to be placed through the bore of a hollow needle 300. Additionally or alternatively, the guidewire 100 is configured to be placed retrograde through a ureteroscope using ultrasound or fluoroscopic guidance. Referring to FIG. 3, in order to facilitate placement with no image guidance, the guidewire 100 comprises markings 110 that help the surgeon determine the position of the guidewire 100. In an embodiment, the guidewire 100 comprises a first mark indicating a distance from a patient's kidney to the ureteral orifice. The guidewire 100 may also comprise additional marks placed at regular intervals above and below the first mark enabling the surgeon to deduce the position of the wire with respect to the kidney. In an embodiment, the first mark is designed to be more prominent (e.g., wider, longer, differently colored) than the additional marks. Placement of the first mark may be based on standardized tables and physiologic measurements of each individual patient. In an embodiment, the standardized tables may be generated by measuring average distance of the kidney from the ureteral orifice for a predefined number of patients. The standardized tables may be correlated with other physiologic characteristics of a patient such as height, weight, sex, or a combination thereof.

Some reduced radiation procedures may require a dark or dim operating room. Accordingly, in an embodiment, the reduced radiation kit comprises a guidewire having marks 110 that can be easily perceived in low light. For example, the marks may comprise a fluorescent material or include a portion that can be perceived by touch.

In an embodiment, the reduced radiation kit comprises a dual-lumen catheter for placement of a safety guidewire alongside a standard guidewire. As is known, a dual lumen catheter is a long, flexible medical device that consists of one hollow tube within another hollow tube, and enables two different actions to take place close together and with less tissue trauma. These actions could be the withdrawal of fluid or the insertion of fluid, air or small medical devices. These catheters can be used to drain blood, urine or unwanted liquid, such as from the lungs or abscesses. A double lumen catheter can be made from one of many flexible materials, such as silicone, latex, Teflon® or polyurethane. In an embodiment, the dual-lumen catheter included in the reduced radiation kit comprises a radio-opaque tip that can be easily visualized with much reduced current (mA) and voltage (kVp) settings on a fluoroscopy machine.

In an embodiment, the reduced radiation kit comprises an extra-stiff guidewire that may comprise a flexible or floppy region at one or both ends of the extra-stiff guidewire, with the flexible or floppy region(s) being more flexible (or less rigid) than an intermediate region. This is a standard component or can be designed as is known to those of skill in the art. Various medical procedures requiring a guidewires use both extra-stiff guidewires as well as standard guidewires. Usually, a soft/floppy guidewire is first inserted through a required body lumen. Then a catheter is positioned over the wire and safely placed in the body lumen. Next, the soft guidewire is removed and the stiff guidewire is threaded through the catheter, to act as a guide for using various medical instruments to perform a medical procedure. A soft guidewire cannot be used as a guide for the medical instruments, as it bends and takes the shape of the body lumen. Hence, the stiff portion of the guide wire provides pushability (due to its rigidity and column strength) while the flexible end(s) provide flexibility and maneuverability in an atraumatic way, minimizing the likelihood of organ puncture/perforation. In an embodiment, the guidewire comprises an angular tip that increases the steerability of the guide wire. In embodiments, a flexible region is placed within 3 to 5 cm from a distal end of the guidewire and the length of the flexible region ranges from 1 to 15 cm. In embodiments, a flexible region is placed within 1 to 2 cm from a proximal end (that is inserted into a body lumen) of the guidewire.

In an embodiment, the extra-stiff guidewire comprises a radio-dense core that allows visualization at extremely low radiation exposure. The extra-stiff guidewire can be configured to be detected at fixed, intentionally-reduced mA and kVp settings ranging from 1 to 8 pps. In an embodiment, the extra-stiff guidewire is configured to be detected at a mA setting ranging from approximately 1.5 mA to approximately 4 mA and at a kVp setting ranging from approximately 50 kVp to approximately 100 kVp. Depending on the size of a patient and on whether a small body part (e.g., finger) is being imaged with fluoroscopy, the extra-stiff guidewires may be detected at even lower mA and kVp settings. In an embodiment, the extra-stiff guidewire is wound with a coating that can be easily detected by ultrasound. Additionally or alternatively, the extra-stiff guidewire is etched with a substance that is easily detected by ultrasound. Additionally or alternatively, the extra-stiff guidewire is coated with a radio-dense coating that is easy to see under reduced fluoroscopy settings. In an embodiment, the extra-stiff guidewire comprises a standard guidewire and an angle-tipped guidewire with similar features. The angular tip increases the steerability of the guide wire, and minimizes trauma to a patient's organs.

In an embodiment, the reduced radiation kit comprises an ultrasound contrast material that is injected through an endhole catheter to help identify the location of the renal pelvis and calices without any radiation exposure. In embodiments, the contrast material comprises air bubbles, such as but not limited to microbubbles, trapped in a biologically safe coating to keep the bubbles in suspension. In an embodiment, bubbles are obtained by having a skilled person inject air into a kidney's collection system. The bubbles aid in increasing the echogenicity of the contrast material, and since, air bubbles tend to rise up, they aid with determining and conveying an orientation of the patient. Additionally or alternatively, the kit comprises a standard ultrasound contrast. In embodiments, the kit comprises an ultrasound contrast already approved for use for injecting into a collecting system.

Figure 4:
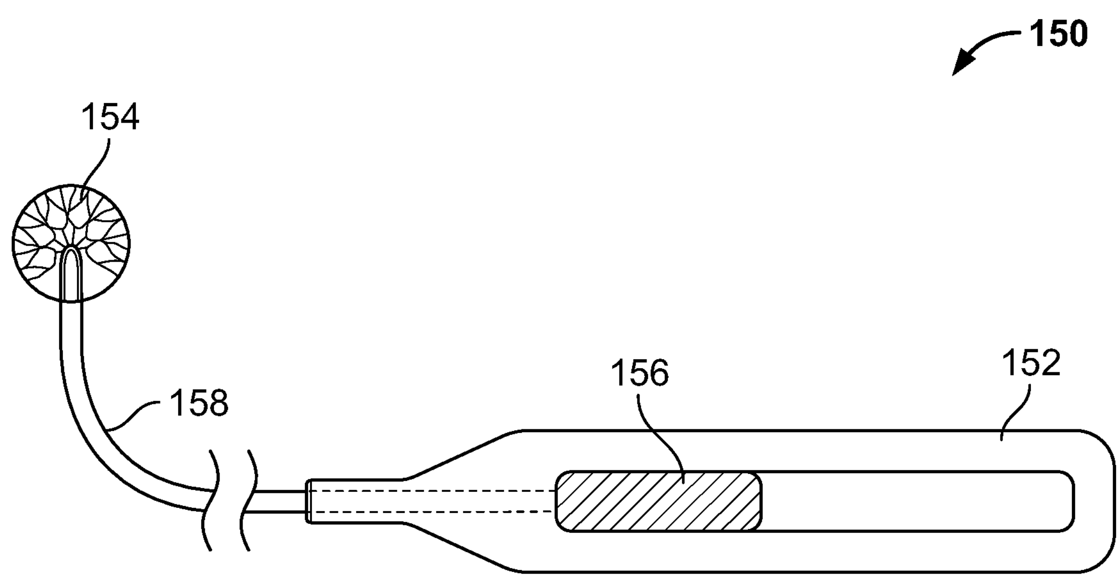
FIG. 4 illustrates an exemplary basket catheter provided in the reduced radiation kit, in accordance with an embodiment of the present specification.

Referring to FIG. 4, in an embodiment, the reduced radiation kit comprises a basket catheter 150. The basket catheter 150 comprises a handle 152 at a proximal end and a basket 154 at a distal end. The basket catheter 150 comprises an actuation member 156 configured to advance and retract the basket 154 relative to an outer sheath 158. The basket 154 is in an open configuration, when advanced distally beyond the outer sheath 158. The open configuration of the basket 154 facilitates insertion of a guidewire into the basket 154. The basket 154 is retracted back into the outer sheath 158 after insertion of the guidewire, thereby closing the open configuration of the basket 154 and capturing the inserted guidewire.

In an embodiment, the basket catheter 150 comprises a 2.2 Fr basket 154 for snaring a small wire ureteroscopically and pulling the wire down into the ureter. In embodiments, the reduced radiation kit comprises a basket 154 such as the 2.2 or 2.4 Fr N-circle basket. Additionally or alternatively, the reduced radiation kit comprises a basket catheter 150 including any of the features disclosed in U.S. Pat. No. 9,095,361, entitled "METHODS AND APPARATUSES FOR FLUORO-LESS OR NEAR FLUORO-LESS PERCUTANEOUS SURGERY ACCESS," filed on Jun. 3, 2014, which is included herein in its entirety. In an embodiment, the basket catheter 150 is used to capture a guidewire with an enhanced ultrasonic profile, such as the guidewire 100 described with reference to FIG. 3. In some aspects of the reduced radiation percutaneous method disclosed herein, the basket catheter 150 is inserted into the patient and opened, making the basket 154 easily seen under ultrasound. A needle 300 (see FIG. 2) is then inserted into the center of the basket 154 under ultrasound. In an embodiment, the needle 300 comprises one or more feature that enhances the ultrasonic profile of the needle 300, thereby facilitating placement of the needle 300 within the basket. A guidewire 100 is then advanced through the needle 300 and into the basket 154. The basket 154 is then closed, thereby capturing the guidewire 100.

Figure 5:
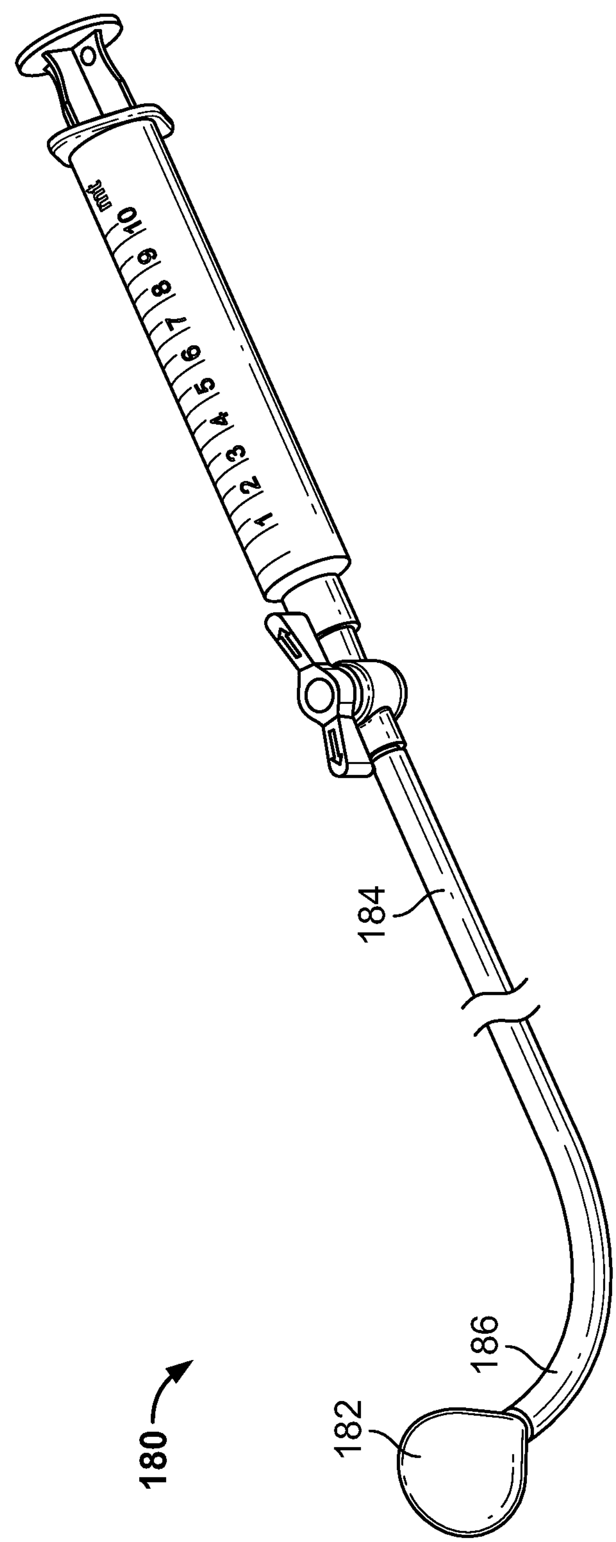
FIG. 5 illustrates an exemplary balloon catheter provided in the reduced radiation kit, in accordance with an embodiment of the present specification.

Referring to FIG. 5, in an embodiment, the reduced radiation kit comprises a balloon catheter 180. In an embodiment, the balloon catheter 180 is a latex-free 22 Fr balloon catheter. In another embodiment, balloon catheter 180 comprises a balloon 182 having diameter ranging from 4 Fr to 24 Fr and made of materials such as, but not limited to latex, silicone, or a radiodense material, thereby facilitating visualization of the balloon 182 under reduced radiation settings. In other embodiments, the diameter of the balloon catheter 180 varies, depending on the body site being accessed. In an embodiment, the balloon catheter 180 is configured to be placed over a guidewire. In an embodiment, the balloon catheter 180 comprises marks (not shown in FIG. 5) along its shaft 184 to facilitate placement of a distal end 186 of the balloon catheter 180 in the calyx of a patient. Additionally or alternatively, the balloon catheter 180 comprises a material that is acoustically dense to facilitate placement of the catheter in the patient's kidney using ultrasound.

In an embodiment, the reduced radiation kit comprises a nephrostomy tube having a diameter ranging from 6 to 10 French that is etched to allow placement of the tube under ultrasound guidance. This is a standard component or can be designed as is known to those of skill in the art. In another embodiment, the reduced radiation kit comprises a nephrostomy tube having a diameter ranging from 4 to 24 Fr for placement in a patient's kidney. Additionally or alternatively, the nephrostomy tube comprises a coating that allows it to be seen under ultrasound. In an embodiment, the nephrostomy tube comprises a tip that includes a radiodense material, making the tip easily visualized under minimal radiation settings.

In an embodiment, the reduced radiation kit comprises a nephrostomy tube sheath having centimeter marks on the outside of the nephrostomy tube sheath, thereby facilitating placement of a corresponding nephrostomy tube at an appropriate depth. This is a standard component or can be designed as is known to those of skill in the art. In an embodiment, the nephrostomy tube sheath comprises a tip that includes a radio-dense material, allowing the internal tip of the sheath to be more easily seen under ultrasound guidance to allow placement of the nephrostomy tube at the appropriate depth.

In an embodiment, the reduced radiation kit comprises a balloon dilator that has radio-opaque marks along its side. The balloon dilator is configured for establishing a tract into a patient's kidney during PCNL or for dilating a patient's ureter during ureteroscopy. In an embodiment, a diameter of the balloon dilator used for dilating the ureter ranges from 12 to 18 Fr and that used for dilating the kidney tract ranges from to 16 to 34 Fr. The balloon catheter 180 comprises a readily visible mark so that a surgeon can perceive the mark under ureteroscopy, thereby facilitating placement of the balloon catheter 180 at the appropriate depth to achieve dilation of the kidney tract.

In an embodiment, the reduced radiation kit comprises a 6 Fr open-ended stent that has marks placed on its external surface. In an embodiment, the kit comprises an acoustically dense JJ ureteral stent that can easily be seen under ultrasound. Additionally and alternatively, the ends of the JJ stent comprise one or more radio-dense materials so that the stent tip can be localized with an adhesive marker placed over the kidney to allow the stent to be positioned with extremely low current (mA) and voltage (kVp) fluoroscopy settings (e.g., settings that enable visualization at fixed intentionally reduced radiation settings at one pulse per second pulsed fluoroscopy). In an embodiment, the stent comprises a mark at the probable location of the ureteral orifice, thereby simplifying placement of the stent with minimal radiation.

Additionally or alternatively, the kit comprises a 5 Fr endhole catheter. In an embodiment, the catheter and the stent described above are acoustically dense and visible under reduced fluoroscopy settings.

In an embodiment, the kit comprises a glide catheter configured to be advanced beyond impacted stones in a kidney during a PCNL procedure. A glide catheter (or "glidecath") provides the enhanced lubricity needed to facilitate smooth atraumatic passage through tortuous anatomy. In an embodiment, a standard glide catheter is modified to allow for facile insertion and placement of the glide catheter using reduced fluoroscopy and ultrasound.

In an embodiment, the kit comprises an advancer for advancing the stent. In an embodiment, the advancer comprises marks along its surface enabling the surgeon to know how far into a urethra the advancer has progressed, thereby allowing placement of a stent using external cues. For example, the distance from the external meatus to the position of the bladder neck is measured on a cytoscope at the start of a procedure. The cytoscope comprises marks to indicate the length of the urethra. Then the stent is placed from outside the urethra over the wire and the advancer used to advance the stent to the correct distance.

In various embodiments, users can tailor the reduced radiation kit based upon individual needs. For example, a user may select the kit items for allowing insertion of an 18 gauge needle followed by insertion of an angle-tipped lubricious wire. Alternatively, a user may select the kit items for insertion of a 19 to 21 gauge needle followed by a small 0.018 inch or 0.025 inch guidewire, which is subsequently upsized over a sheath to a size that can allow placement of a 0.038 inch wire once correct positioning of the needle is confirmed. As discussed above, these wires comprise features such as markings indicating how far the wire has progressed inside the patient.

Figure 6A:
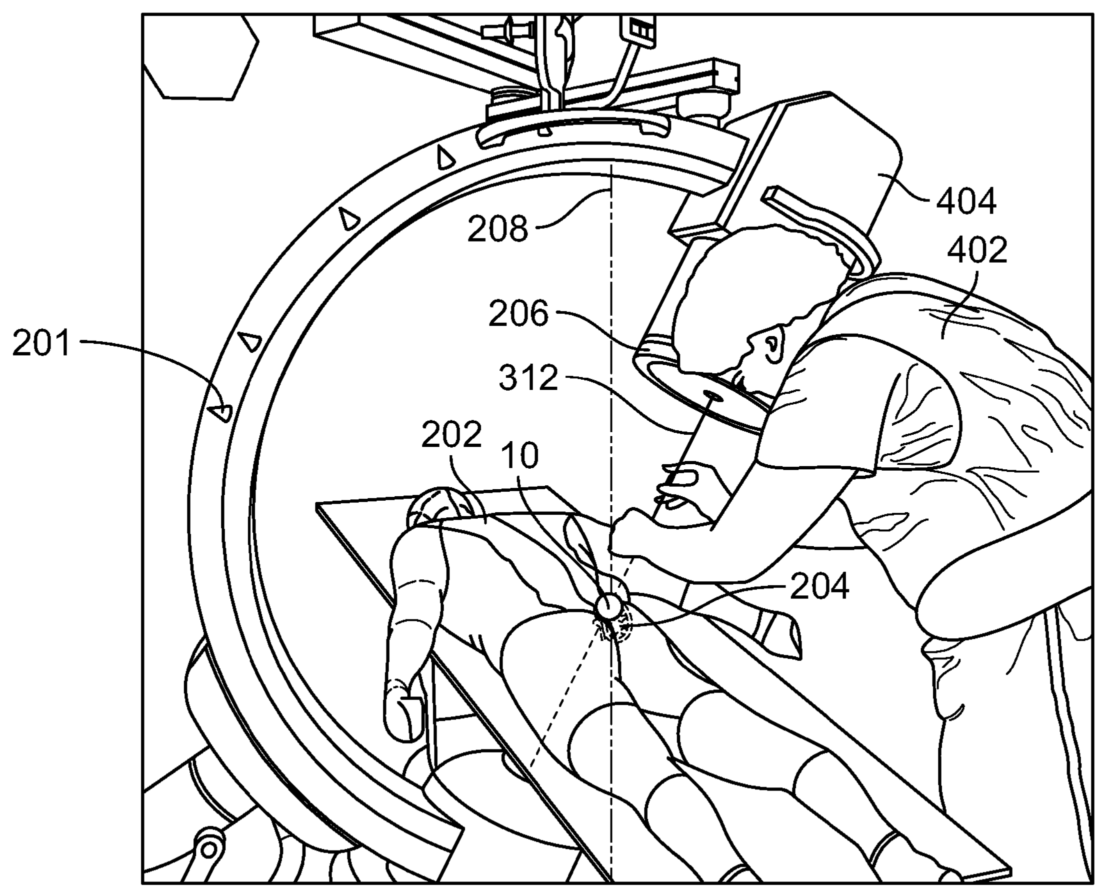
FIG. 6A illustrates a reduced radiation percutaneous needle access procedure being performed by using the reduced radiation kit, in accordance with an embodiment of the present specification.
Figure 6B:
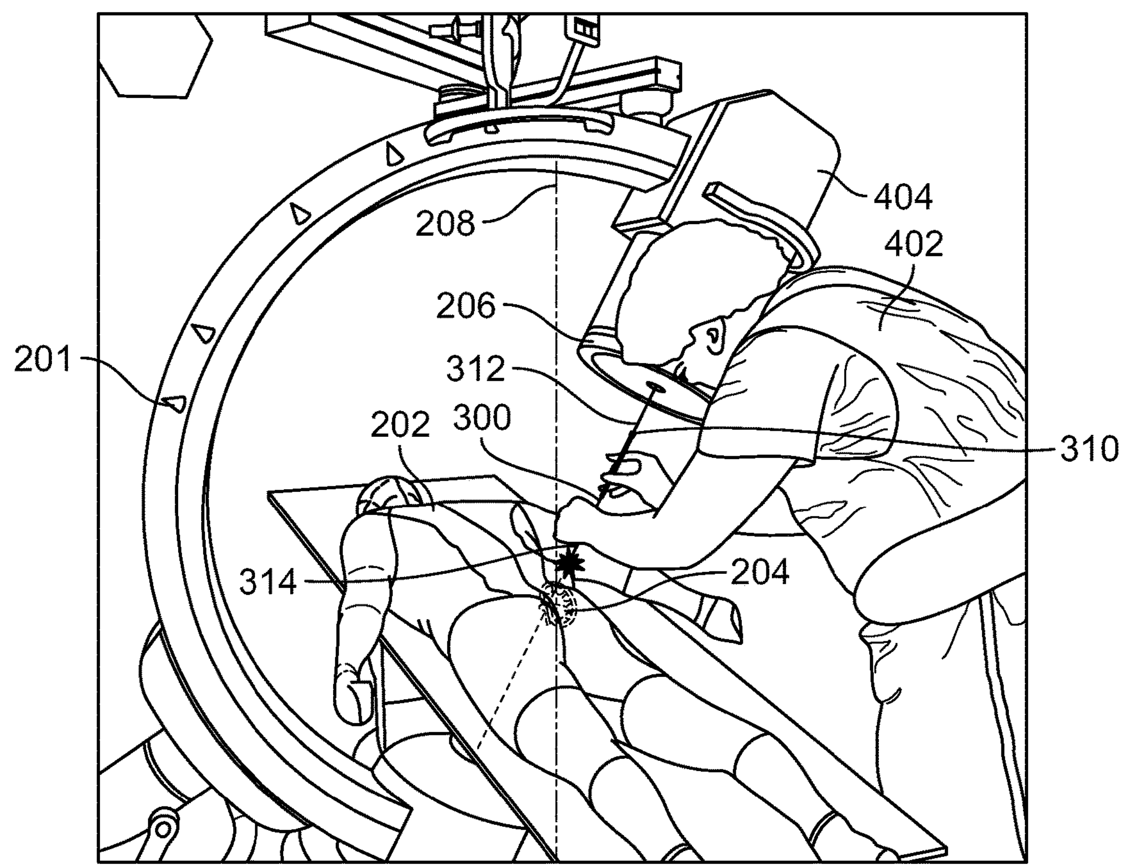
FIG. 6B illustrates another step of the reduced radiation percutaneous needle access procedure of shown in FIG. 6A.

In an embodiment, as shown in FIGS. 6A-6D, the reduced radiation kit of the present specification is used to perform a reduced radiation percutaneous needle access procedure (e.g., percutaneous nephrolithotomy). For example, as shown in FIG. 6A, a reduced radiation percutaneous needle access procedure is being performed by a surgeon 402 by using a using a C-arm 201 comprising a head 404 coupled with a laser guide 206. The laser guide 206 is configured to facilitate the alignment and insertion of a needle 300 (see FIGS. 6B-6D) without fluoroscopy or with decreased fluoroscopy and without other image guidance. The laser guide 206 is directed at a desired needle-insertion angle, for example, in line with a sticker 10 or other marker placed on the body of a patient 202, and a ureteroscope (not shown) placed inside a desired calix of the patient's 202 kidney 204 that is selected for puncture. In an embodiment, the desired needle-insertion angle is zero degrees and/or less than or equal to about 45 degrees relative to a vertical axis 208. In an embodiment, the insertion angle ranges from 0 degrees to 30 degrees. In another embodiment, the insertion angle ranges from 15 degrees to 45 degrees, and is approximately 30 degrees.

After the laser guide 206 is directed at the desired access location and angle, a needle hub 310 (shown in FIG. 6B and FIG. 2) is aligned with the laser beam 312 that is emitted from the laser guide 206. Once the needle hub 310 is aligned with the laser beam 312, such that the needle hub 310, needle tip 314 (shown in FIG. 2), and ureteroscope tip (not shown) within the patient's 202 kidney 204 form a single point trajectory on the C-arm 201 (shown in FIG. 6C), the surgeon may insert the needle 300 without any fluoroscopy activation or with greatly minimized fluoroscopy exposure used only to adjust for slight variations in respiratory excursion (shown in FIG. 6D).

Figure 6C:
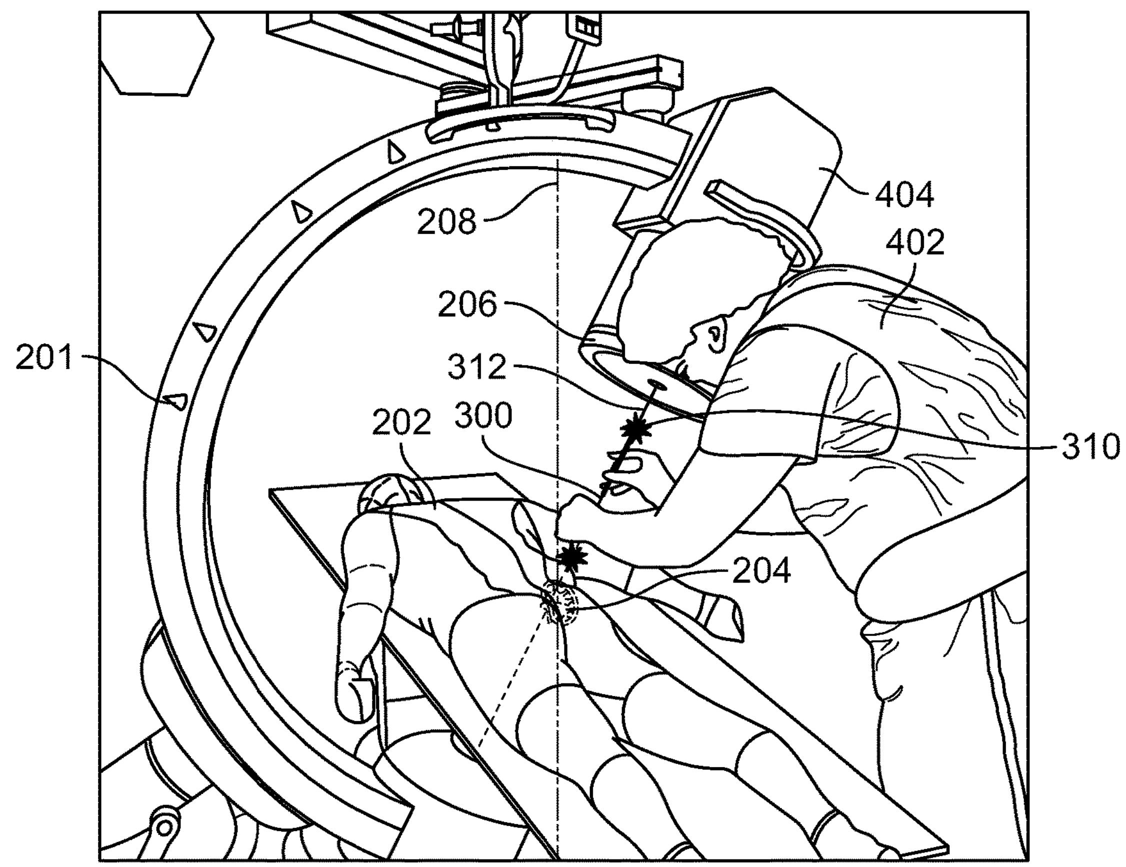
FIG. 6C illustrates another step of the reduced radiation percutaneous needle access procedure of shown in FIG. 6A.
Figure 6D:
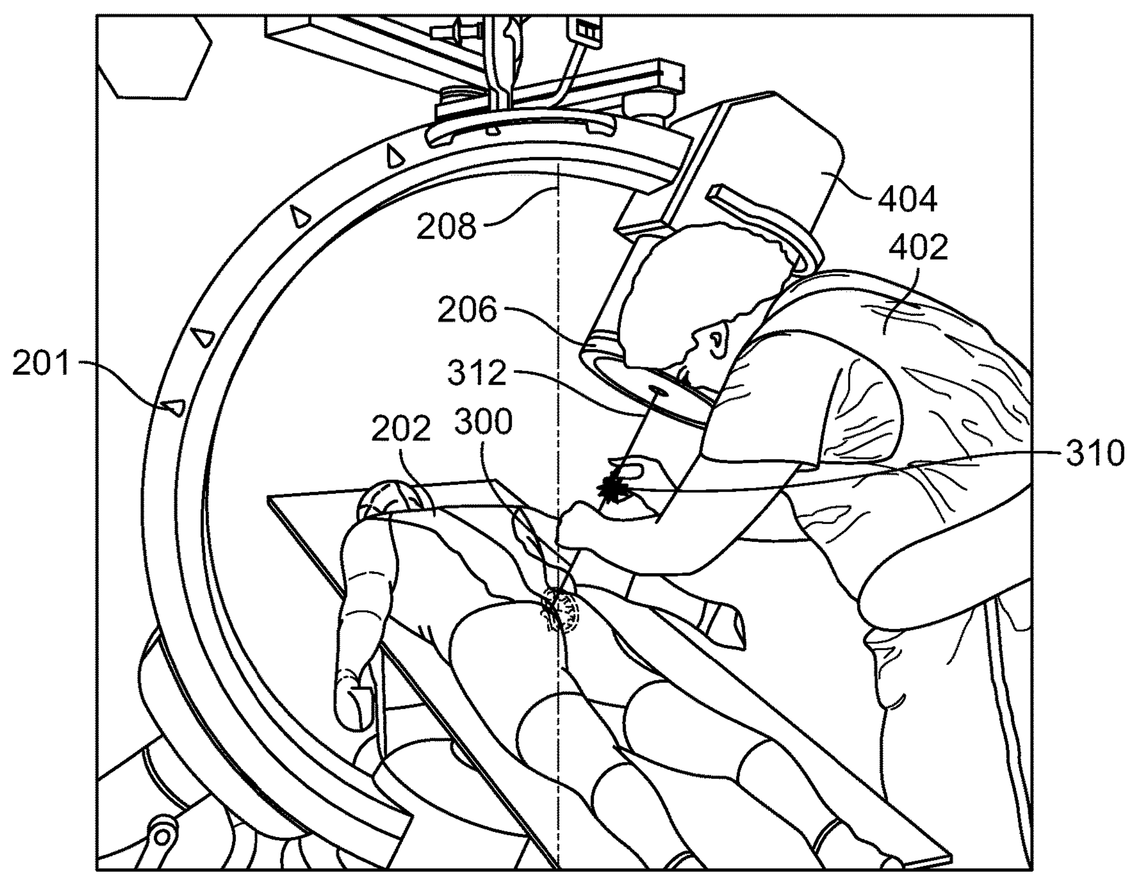
FIG. 6D illustrates another step of the reduced radiation percutaneous needle access procedure of shown in FIG. 6A.

As shown in FIG. 6C, the laser beam 312 is centered on the hub 310 of the needle 300, such that the hub 310 is illuminated, ensuring that the needle 300 is inserted at a predefined trajectory. The depth of insertion can be determined based on a pre-operative CT scan or ultrasound measurements where the depth from the skin to the desired calix was measured. Alternatively, the desired depth of insertion is marked on the needle 300 based on the initial images of the target using a mark or removable clip, tape or bracket. The bracket is attached to the needle 300 reversibly so that the needle would be inserted the desired depth, on the desired trajectory as directed by the laser beam 312. Once at the desired depth the bracket is removed.

Once the needle 300 has been inserted, the C-arm 201 is rotated and activated with a single pulse to confirm the depth of the needle 300. The C-arm 201 is rotated to an angle that is on the opposite side of the vertical axis 208 from the needle insertion angle. The angle can be equal to the needle insertion angle. For example, if the desired insertion angle is about 30 degrees, the C-arm 201 is rotated 60 degrees, such that the C-arm 201 is positioned 30 degrees relative to the vertical axis 208 opposite the needle insertion angle. Usually, if the C-arm 201 is rotated 30 degrees toward the surgeon, the depth of the needle 300 within the kidney 204 is checked by rotating the C-arm 201 to 30 degrees away from the surgeon. Additionally or alternatively, the surgeon can judge the depth of the needle 300 within the kidney 204 by watching the ureteroscope's image to determine under direct vision when the needle 300 enters a collecting system.

With the needle 300 in place, a wire is passed from the insertion needle 300 into the collecting system. The direct endoscopic vision of the internal tip 314 of the needle 300 facilitates placement of the guidewire 100.

In an embodiment, an end of the guidewire 100 is grasped with a basket 154 (shown in FIG. 4) passed in a retrograde fashion through the ureteroscope and used to grasp the guidewire 100 as described above. This basket 154 is used to pull the wire down the patient's 202 ureter (not shown) to establish through and through access out the patient's 202 urethra, or alternatively to establish access only into the proximal ureter beyond the level of any stone or obstruction.

In an embodiments, a ureteral access sheath is placed in a retrograde fashion using a completely fluoro-less or minimal fluoroscopy technique. This ureteral access sheath allows the ureteroscope to be re-inserted into the kidney multiple times.

After positioning the guidewire 100, the guidewire 100 is converted to a conventional or stiff wire for subsequent dilation of the tract from the skin into the collecting system of the kidney 204. The patient's 202 skin is incised with a scalpel to a desired size depending on the size of a sheath being employed for dilation. Next, a dilating balloon or serial dilation device is placed at a desired depth using the ureteroscope under direct vision to avoid the use of fluoroscopy.

In embodiments, the ureteroscope is used to watch the tip of the balloon catheter 180 enter the collecting system of the kidney 204 and then to position the dilating balloon or serial dilator so that the maximal dilation occurs just inside the edge of the kidney's 204 caliceal collecting system. The desired depth may be determined on a first of a serial dilator, if serial dilation is to be performed. The determined depth is used to insert the subsequent dilators using a bracket, using preplaced markings placed upon the dilators or a mark placed upon the dilators during surgery. If a balloon 182 (shown in FIG. 5) is used for dilation, the balloon 182 is inflated to the appropriate pressure for full dilation, and the sheath is placed into the kidney under direct ureteroscopic visualization. Alternatively, fluoroscopy could be used to position the sheath in a conventional manner or using a reduced fluoroscopic technique.

With the correct position of the sheath confirmed ureteroscopically, the procedure to remove one or more stones from the kidney 204 may be performed in a conventional fashion. In embodiments, flexible and rigid nephroscopy accompanied by use of ultrasound, laser, and/or basketing are used to remove the stone fragments. At the conclusion of the procedure, the kidney 204 is evaluated by flexible nephroscopy and ureteroscopy to confirm the absence of residual fragments. Intraoperative ultrasound can also be used to look for residual stones.

After the removal of all stones, a single pulse of conventional fluoroscopy is used to ensure complete fragment removal. This step is omitted if the surgeon 402 is sure there are no residual fragments following endoscopic renal mapping. Alternatively, renal ultrasound could is used to look for residual fragments.

If a tubeless technique is desired, the surgeon 402 removes all the tubes at the conclusion of the procedure. Alternatively, the surgeon places an 8 or 10 Fr nephrostomy, or a 16, 18, or 22 Fr council-tipped catheter with a 5 Fr re-entry catheter inside the patient's 202 renal tract to allow for renal drainage and reentry at a later time if desired. These tubes are placed entirely without image guidance using direct vision by the ureteroscope or with minimal use of single pulse fluoroscopy. In another embodiment, the ureteral catheter is placed into the kidney 204 from above while monitoring the position of a proximal end of the catheter using a flexible nephroscope placed through the percutaneous access site.

In some embodiments, a ureteral stent (e.g., a multi-length stent having a length ranging from 22 cms to 32 cm and/or a diameter of approximately 6 Fr) is passed over a guidewire 100 that was placed into the bladder using an angle tipped guidewire 100 and a 4 Fr glide catheter. In another configuration, the 0.038 guidewire is used to insert the stent. In an embodiment, the length of the stent is calculated using a novel technique determining the ureteral length using the Pythagorean Theorem where ureter length is calculated by measuring the known coronal ureter length, left to right length, and anterior/posterior length. Alternatively, the length is estimated by counting the number of axial slices on a CT scan and multiplying by the slice reconstruction and adding 20%. In this technique, the fixed length stent is placed into the ureter from above and the stent is advanced until the markings showing the location for the UPJ are identified. The distal stent coil in the bladder is confirmed when the ureteroscope is pulled down into the bladder.

In an embodiment, an end-hole catheter is placed cystoscopically into the ureter and used to inject diluted contrast into the collecting system of the kidney ranging from 1-99% dilution depending upon the desired density of the contrast. The desired calyx is selected using fluoroscopy and any of the previously described techniques mentioned in the preceding description could be used for establishing access into the kidney. For example, in an embodiment, the C-arm 201 is rotated laterally between 20 and 30 degrees. The C-arm 201, sticker 10, and desired calyx are aligned, and the laser guide 206 is placed in the center of the needle hub 310 and used to insert the needle 300 in a steady controlled fashion. Using this technique, the surgeon can use his hands with no concern of radiation exposure since the laser guide 206 is used to direct the needle 300. Aspiration of fluid or air is used to confirm appropriate positioning in the calyx. Thereafter, a lubricious wire is fed down the ureter using minimal use of low-dose pulsed or conventional fluoroscopy.

In an embodiment, an ultrasound machine is used to select percutaneously the appropriate desired posterior calyx for access. The laser guide 206 is positioned in line with the access of the ultrasound guide. Alternatively, a separate laser guide 206 is lined up with the axis of the ultrasound guide for insertion of the probe.

In an embodiment, a laser guide 206 is placed on a CT scanner or a CT fluoroscopy machine and the axis of the needle tract is positioned in line with the laser guide 206 as directed by the CT scanner.

In another embodiment, the laser guide 206 is placed on a CT scanner and a special non-ferromagnetic needle is used for placement using CT fluoroscopy.

At various points of the procedure, fluoroscopy is performed either with a single pulse or a pulse rate of one pulse per second to visualize the tip of the ureteroscope, needle 300, and/or guidewire 100. This pulse rate is lower than the conventional pulse rate, which ranges from 25 to 30 pulses per second. The method of the present specification enables a surgeon to reduce the fluoroscopy time from an average of approximately 6 to 7 minutes per procedure to less than about one minute per procedure. In certain aspects, the total fluoroscopy time is less than or equal to ten seconds, less than or equal to three seconds, or less than or equal to 1 second, thus reducing the risk of cancer for the patient, surgeon and staff by reducing the radiation exposure.

Figure 7:
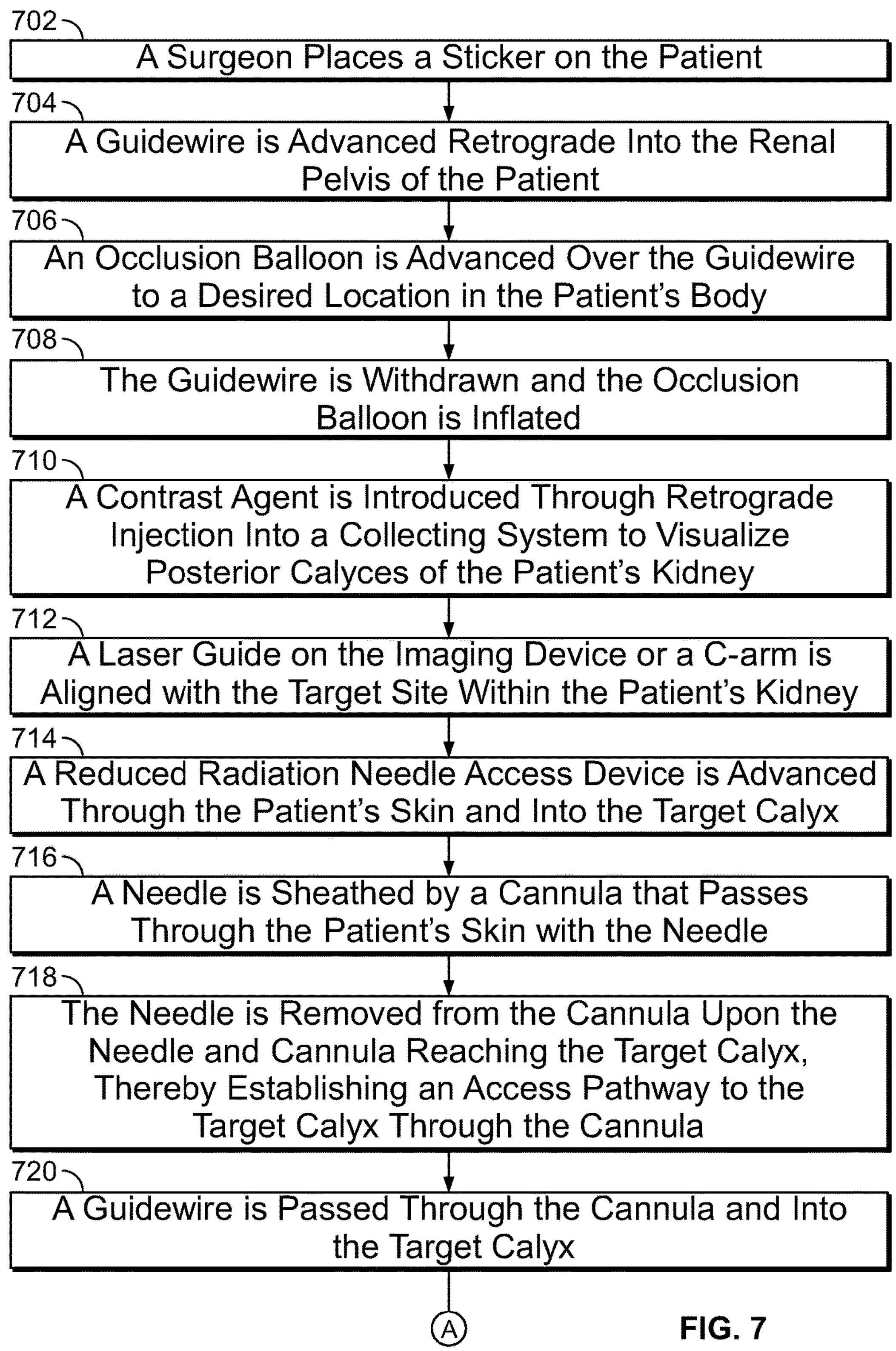
FIG. 7 is a flowchart illustrating an exemplary method of performing a reduced radiation percutaneous needle access procedure by using the reduced radiation kit, in accordance with an embodiment of the present specification.
Figure 7:
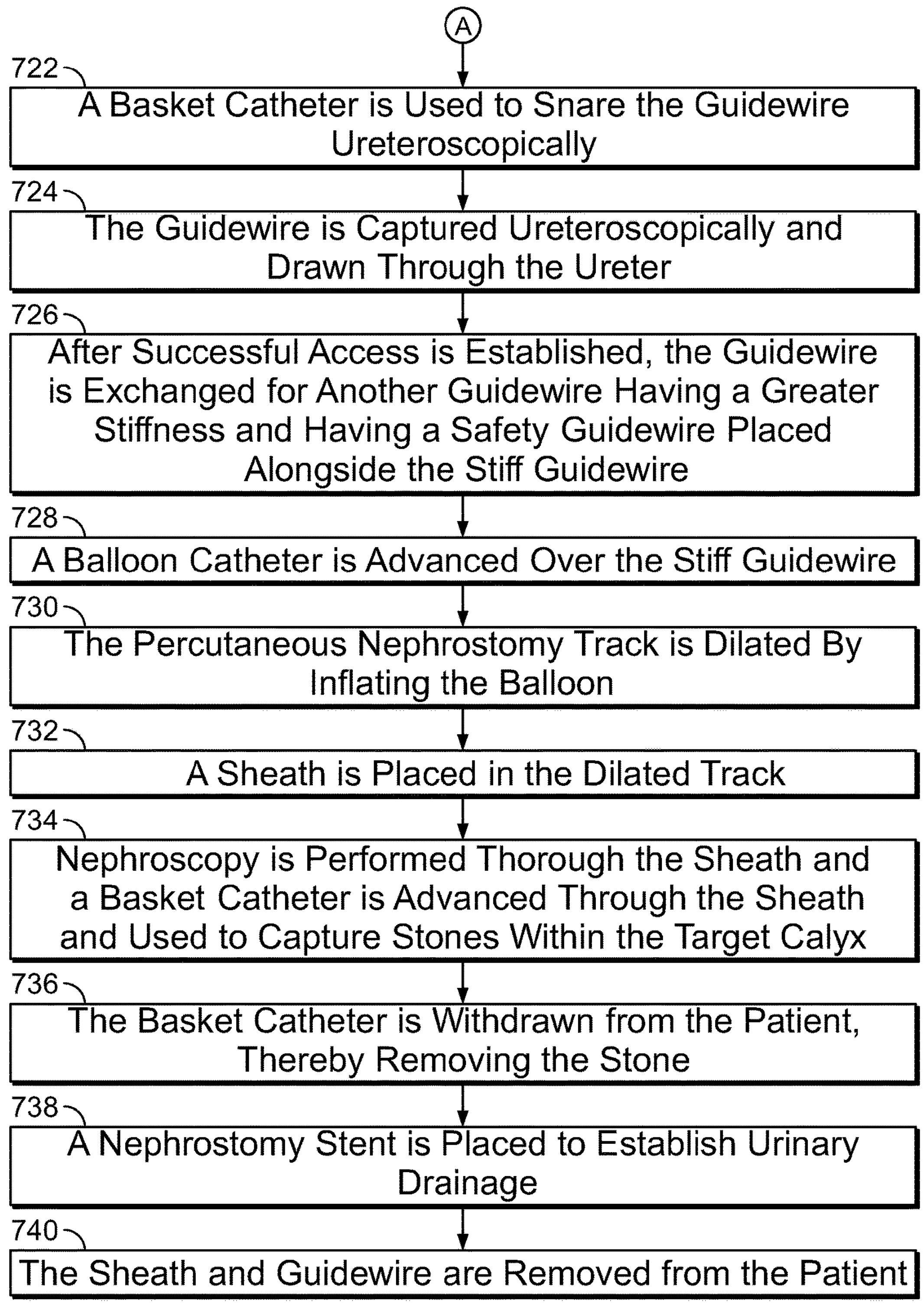

FIG. 7 is a flowchart illustrating an exemplary method of performing a reduced radiation percutaneous needle access procedure on a patient by using the reduced radiation kit, in accordance with an embodiment of the present specification. In an embodiment, a reduced radiation percutaneous needle access procedure is a percutaneous nephrolithotomy (PCNL) procedure involving placement of a needle through the patient's skin into the kidney for access into one of the calices of the kidney for removing kidney stones.

At step 702 a surgeon places a sticker on the patient either directly on the skin of the patient prior to placing drapes over the patient, or after the drapes has been placed by palpating physiologic landmarks on the patient's body. Additional stickers may be placed on the patient's skin to identify the location of other internal organs. At step 704, a guidewire is advanced retrograde into the renal pelvis of the patient. At step 706, an occlusion balloon is advanced over the guidewire to a desired location in the patient's body (e.g., within the ureter near the renal pelvis). At step 708, the guidewire is withdrawn and the occlusion balloon is inflated. At step 710, a contrast agent is introduced through retrograde injection into a collecting system to visualize posterior calyces of the patient's kidney. In an embodiment, the contrast agent is an ultrasound contrast agent and the calyces are visualized using ultrasound technique. At step 712, a laser guide on the imaging device or a C-arm is aligned with the target site within the patient's kidney. At step 714, a reduced radiation needle access device is advanced through the patient's skin and into the target calyx. In an embodiment, the sticker comprises a recess or opening to accommodate passage of the needle. Additionally or alternatively, the sticker comprises a radiopaque circle having a hollow center that the surgeon can target the needle through.

In an embodiment, at step 716 a needle is sheathed by a cannula that passes through the patient's skin with the needle. The laser guide is used to maintain alignment of the needle as the needle is advanced into the target calyx. At step 718 the needle is removed from the cannula upon the needle and cannula reaching the target calyx, thereby establishing an access pathway to the target calyx through the cannula. At step 720, a guidewire is passed through the cannula and into the target calyx. At step 722, a basket catheter is used to snare the guidewire ureteroscopically. At step 724, the guidewire is captured ureteroscopically and drawn through the ureter. At step 726, after successful access is established, the guidewire is exchanged for another guidewire having a greater stiffness and having a safety guidewire placed alongside the stiff guidewire. In an embodiment, the needle is inserted into the calyx and then advanced past a stone in the patient's kidney into the ureter using fluoroscopy or ultrasound guidance.

At step 728, a balloon catheter is advanced over the stiff guidewire. At step 730 the percutaneous nephrostomy track is dilated by inflating the balloon. At step 732 a sheath is placed in the dilated track. At step 734, nephroscopy is performed thorough the sheath and a basket catheter is advanced through the sheath and used to capture stones within the target calyx. At step 736, the basket catheter is withdrawn from the patient, thereby removing the stone. At step 738, a nephrostomy stent is placed to establish urinary drainage. At step 738, the sheath and guidewire are removed from the patient.

Figure 8:
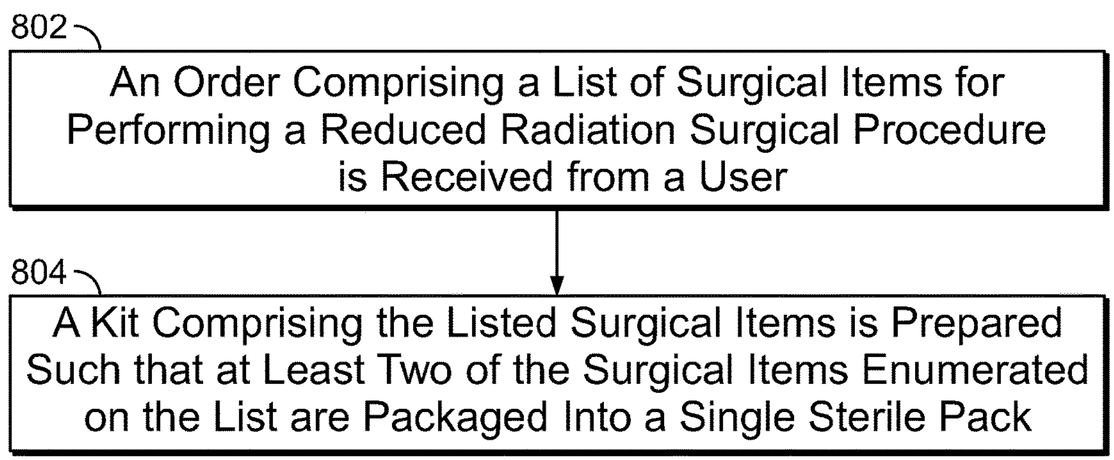
FIG. 8 is a flowchart illustrating a method of making a reduced radiation kit for performing a reduced radiation percutaneous procedure, in accordance with an embodiment of the present specification.

FIG. 8 is a flowchart illustrating a method of making a reduced radiation kit for performing a reduced radiation percutaneous procedure, in accordance with an embodiment of the present specification. At step 802 an order comprising a list of surgical items for performing a reduced radiation surgical procedure is received from a user. In an embodiment, the surgical items are selected from a group consisting of a guidewire, a needle, a sticker, a balloon catheter, a stent, a sheath, a contrast agent, and a basket catheter. At step 804 a kit comprising the listed surgical items is prepared such that at least two of the surgical items enumerated on the list are packaged into a single sterile pack. The surgical items are "reduced radiation surgical items" because the surgical items are adapted for use in a reduced radiation application.

The above examples are merely illustrative of the many applications of the system of present specification. Although only a few embodiments of the present specification have been described herein, it should be understood that the present specification might be embodied in many other specific forms without departing from the spirit or scope of the specification. Therefore, the present examples and embodiments are to be considered as illustrative and not restrictive, and the specification may be modified within the scope of the appended claims.

I claim:

1. A kit for performing a reduced radiation percutaneous procedure, the kit comprising:
- a needle access device comprising:
  - a needle connected to a hub portion, the hub portion comprising:
    - an opaque cap portion;
    - a non-opaque body portion positioned between the opaque cap portion and the needle; and
    - a channel extending through the opaque cap portion, the channel positioned such that the non-opaque body portion only illuminates when a light source is aligned with the channel;

a sticker comprising:

an adhesive side adapted to adhere to the skin of a patient; and a display surface opposite the adhesive side, the display surface being configured to enhance visualization of the sticker in low light, the sticker being configured to designate a portion of skin through which the needle should pass to be in alignment with a target site, wherein the sticker comprises an opening adapted to allow the needle to penetrate the portion of skin via the opening and not by penetrating a surface of the sticker; and a guidewire comprising:

a flexible portion comprising a distal end;

an intermediate region coupled to the flexible portion, wherein the intermediate region is more rigid than the flexible portion; and an ultrasonic-profile-enhancing feature disposed within 3 centimeters of the distal end of the flexible portion.

2. The kit according to claim 1 further comprising an item selected from the group consisting of a balloon catheter, a nephrostomy tube, an ultrasound contrast agent, and a stent.

3. The kit according to claim 2 wherein the item includes a feature to enhance the ultrasonic profile of the item.

4. The kit according to claim 1 wherein the kit is packaged in a single sterile pack.

5. The kit according to claim 1 wherein the display surface of the sticker comprises a glow-in-the-dark feature.

6. The kit according to claim 1 wherein the display surface of the sticker comprises a fluorescent material.

7. The kit according to claim 1 wherein the display surface of the sticker comprises a mirrored surface.

8. The kit according to claim 1 wherein the guidewire further comprises a mark on an outer surface of the guidewire, wherein the mark is configured to indicate a distance from a kidney to a ureteral orifice.

9. A method of performing a reduced radiation percutaneous access procedure, the method comprising:

specifying a plurality of reduced radiation surgical items to include in a kit, wherein the kit comprises at least a portion of the plurality of surgical items packaged within a single sterile pack; and using at least one of the plurality of reduced radiation surgical items from the kit to perform a percutaneous procedure, wherein the percutaneous procedure comprises:

identifying a target site within a kidney of a patient;

aligning a laser with the target site;

placing a sticker on a skin of a patient, wherein the sticker is adapted to indicate an area of skin through which a needle must pass to reach the target site when the needle is advanced along a line defined by the laser;

inserting the needle and a cannula through the area of skin indicated by the sticker, the cannula coaxially surrounding the needle;

advancing the needle and the cannula to the target site while keeping the needle in alignment with the line defined by the laser; and, withdrawing the needle from the cannula while leaving the cannula in place, thereby establishing a percutaneous access to the target site.

10. A method of performing a reduced radiation percutaneous access procedure, the method comprising:

specifying a plurality of reduced radiation surgical items to include in a kit, wherein the kit comprises at least a portion of the plurality of reduced radiation surgical items packaged within a single sterile pack; and using at least one of the plurality of reduced radiation surgical items from the kit to perform a percutaneous procedure, wherein the percutaneous procedure comprises:

identifying a target site within an organ of a patient;

aligning a laser with the target site;

placing a sticker on a skin of a patient, wherein the sticker is adapted to indicate an area of skin through which a needle must pass to reach the target site when the needle is advanced along a line defined by the laser;

inserting the needle and a cannula through the area of skin indicated by the sticker, the cannula coaxially surrounding the needle;

advancing the needle and the cannula to the target site while keeping the needle in alignment with the line defined by the laser; and, withdrawing the needle from the cannula while leaving the cannula in place, thereby establishing a percutaneous access to the target site.

11. The method of claim 10, where said plurality of reduced radiation surgical items to include in a kit can be selected from being selected from the group consisting of a guidewire, a needle, a sticker, a balloon catheter, a stent, a sheath, a contrast agent, and a basket catheter.

12. The method of claim 10, wherein said organ is a kidney.

13. The method of claim 11 wherein at least one of the plurality of reduced radiation surgical items includes a feature to enhance the ultrasonic profile of the item.

14. The method of claim 13 wherein the feature to enhance the ultrasonic profile of the item increases the roughness of a portion of a surface of the item relative to a remainder of said surface.

15. The method of claim 10 wherein the kit is packaged in a single sterile pack.

16. The method of claim 10 wherein a display surface of the sticker comprises a glow-in-the-dark feature.

17. The method of claim 10 wherein a display surface of the sticker comprises a fluorescent material.

18. The method of claim 10 wherein a display surface of the sticker comprises a mirrored surface.

19. The method of claim 11 wherein the guidewire further comprises a mark on an outer surface of the guidewire, wherein the mark is configured to indicate a distance from a kidney to a ureteral orifice.

* * * * *